US011375927B2

(12) United States Patent
DeHennis et al.

(10) Patent No.: US 11,375,927 B2
(45) Date of Patent: Jul. 5, 2022

(54) ANALYTE MONITORING SYSTEMS AND METHODS THAT MAKE USE OF INFORMATION ABOUT A CONDITION OF THE ENVIRONMENT SURROUNDING AN ANALYTE SENSOR

(71) Applicant: Senseonics, Incorporated, Germantown, MD (US)

(72) Inventors: Andrew DeHennis, Germantown, MD (US); Xiaoxiao Chen, Washington, DC (US)

(73) Assignee: Senseonics, Incorporated, Germantown, MD (US)

( * ) Notice: Subject to any disclaimer, the term of this patent is extended or adjusted under 35 U.S.C. 154(b) by 225 days.

(21) Appl. No.: 16/675,757

(22) Filed: Nov. 6, 2019

(65) Prior Publication Data

US 2020/0138350 A1 May 7, 2020

Related U.S. Application Data

(60) Provisional application No. 62/756,815, filed on Nov. 7, 2018.

(51) Int. Cl.
*A61B 5/1455* (2006.01)
*A61B 5/00* (2006.01)
*A61B 5/145* (2006.01)

(52) U.S. Cl.
CPC ........ *A61B 5/14552* (2013.01); *A61B 5/0031* (2013.01); *A61B 5/14503* (2013.01); *A61B 5/14532* (2013.01)

(58) Field of Classification Search
None
See application file for complete search history.

(56) References Cited

U.S. PATENT DOCUMENTS

| | | | |
|---|---|---|---|
| 9,414,775 B2 | 8/2016 | Colvin, Jr. et al. | |
| 9,693,714 B2 | 7/2017 | DeHennis et al. | |
| 2011/0236989 A1* | 9/2011 | Suri | G01N 21/6428 436/172 |
| 2011/0295128 A1* | 12/2011 | Yuasa | G01L 9/16 600/485 |
| 2013/0241745 A1 | 9/2013 | Colvin, Jr. et al. | |
| 2015/0141777 A1* | 5/2015 | Emken | A61B 5/14556 600/316 |

* cited by examiner

*Primary Examiner* — Marjan Fardanesh
(74) *Attorney, Agent, or Firm* — Rothwell, Figg, Ernst & Manbeck, P.C.

(57) ABSTRACT

An analyte monitoring system may include an analyte sensor and a transceiver. The analyte sensor may include: a sensor housing, an analyte indicator on at least a portion of the sensor housing, a protective material on at least a portion of the analyte indicator, and a light source in the sensor housing and configured to emit excitation light to analyte indicator. The transceiver may be configured to receive the sensor measurements conveyed by the analyte sensor, infer information about a condition of the environment surrounding the analyte sensor, and calculate an analyte level using at least one or more of the sensor measurements and the inferred information about the condition of the environment surrounding the sensor. The protective material may have a thickness that is thin enough to allow at least some of the excitation light to pass through the protective material and into the environment surrounding the analyte sensor.

22 Claims, 9 Drawing Sheets

ANALYTE MONITORING SYSTEMS AND METHODS THAT MAKE USE OF INFORMATION ABOUT A CONDITION OF THE ENVIRONMENT SURROUNDING AN ANALYTE SENSOR

CROSS-REFERENCE TO RELATED APPLICATION

The present application claims the benefit of priority to U.S. Provisional Application Ser. No. 62/756,815, filed on Nov. 7, 2018, which is incorporated herein by reference in its entirety.

BACKGROUND

Field of Invention

Aspects of the present invention may relate to methods and systems for analyte monitoring. More specifically, some aspects of the present invention may relate to a protective material on an analyte indicator of an analyte sensor of the analyte monitoring that reduces degradation of the analyte indicator while allowing visibility to the environment surrounding the analyte sensor. Some aspects of the present invention may relate to inferring information about a condition of the environment surrounding the analyte sensor and calculating an analyte level using the inferred information.

Discussion of the Background

The prevalence of diabetes mellitus continues to increase in industrialized countries, and projections suggest that this figure will rise to 4.4% of the global population (366 million individuals) by the year 2030. Glycemic control is a key determinant of long-term outcomes in patients with diabetes, and poor glycemic control is associated with retinopathy, nephropathy and an increased risk of myocardial infarction, cerebrovascular accident, and peripheral vascular disease requiring limb amputation. Despite the development of new insulins and other classes of antidiabetic therapy, roughly half of all patients with diabetes do not achieve recommended target hemoglobin A1c (HbA1c) levels<7.0%.

Frequent self-monitoring of blood glucose (SMBG) is necessary to achieve tight glycemic control in patients with diabetes mellitus, particularly for those requiring insulin therapy. However, current blood (finger-stick) glucose tests are burdensome, and, even in structured clinical studies, patient adherence to the recommended frequency of SMBG decreases substantially over time. Moreover, finger-stick measurements only provide information about a single point in time and do not yield information regarding intraday fluctuations in blood glucose levels that may more closely correlate with some clinical outcomes.

Continuous glucose monitors (CGMs) have been developed in an effort to overcome the limitations of finger-stick SMBG and thereby help improve patient outcomes. These systems enable increased frequency of glucose measurements and a better characterization of dynamic glucose fluctuations, including episodes of unrealized hypoglycemia. Furthermore, integration of CGMs with automated insulin pumps allows for establishment of a closed-loop "artificial pancreas" system to more closely approximate physiologic insulin delivery and to improve adherence.

Monitoring real-time analyte measurements from a living body via wireless analyte monitoring sensor(s) may provide numerous health and research benefits. There is a need to enhance such analyte monitoring systems via innovations.

SUMMARY

One aspect of the invention may provide an analyte monitoring system including an analyte sensor and a transceiver. The analyte sensor may include a sensor housing, an analyte indicator, a protective material, a light source, a signal photodetector, a reference photodetector, and a transceiver interface. The analyte indicator may be on at least a portion of the sensor housing and may be configured to emit an amount of light indicative of an analyte level in a first medium in proximity to the analyte indicator. The protective material may be on at least a portion of the analyte indicator and may be configured to reduce degradation of the analyte indicator by catalytically decomposing or inactivating one or more in vivo reactive oxygen species or biological oxidizers. The light source may be in the sensor housing and may be configured to emit excitation light to analyte indicator. The signal photodetector may be in the sensor housing and may be configured to receive light emitted by the analyte indicator and generate a measurement signal indicative of the amount of light emitted by the analyte indicator and received by the signal photodetector. The reference photodetector may be in the sensor housing and may be configured to receive light emitted by the light source and reflected by one or more of the analyte indicator and an environment surrounding the analyte sensor and generate a reference signal indicative of an amount of light received by the reference photodetector. The transceiver interface may be configured to convey sensor measurements including one or more measurements of the measurement signal and one or more measurements of the reference signal. The transceiver may include a sensor interface and a processor. The sensor interface may be configured to receive the sensor measurements conveyed by the analyte sensor. The processor may be configured to infer information about a condition of the environment surrounding the analyte sensor and calculate an analyte level in a second medium using at least one or more of the sensor measurements and the inferred information about the condition of the environment surrounding the sensor. The protective material may have a thickness that is thin enough to allow at least some of the excitation light emitted by the light source to pass through the protective material and into the environment surrounding the analyte sensor.

In some embodiments, inferring the information about the condition of the environment surrounding the analyte sensor may include estimating a healing state of tissue surrounding the sensor. In some embodiments, calculating an analyte level in the second medium using at least the one or more of the sensor measurements and the inferred information about the condition of the environment surrounding the sensor may include: adjusting one or more parameters of a conversion function based on at least the inferred information about the condition of the environment surrounding the sensor, and using the adjusted conversion function and the one or more of the sensor measurements to calculate the analyte level in the second medium. In some embodiments, calculating an analyte level in the second medium using at least the one or more of the sensor measurements and the inferred information about the condition of the environment surrounding the sensor may include: selecting a conversion function based on at least the inferred information about the condition of the environment surrounding the sensor, and using the selected conversion function and the one or more of the sensor measurements to calculate the analyte level in the second medium.

In some embodiments, the protective material may be sputtered on the analyte indicator. In some embodiments, the protective material may include platinum. In some embodiments, the protective material may have a thickness in a range from 1 nm to 20 nm. In some embodiments, the protective material may have a thickness in a range from 3 nm to 6 nm. In some embodiments, the protective material may have a thickness in a range from 8 nm to 12 nm. In some embodiments, the protective material may have a thickness of 10 nm.

In some embodiments, the environment surrounding the sensor may include one or more of tissue, blood, and clotting. In some embodiments, the light received by the reference photodetector may include light that was emitted by the light source, passed through the analyte indicator, and was reflected by tissue outside the analyte sensor.

Another aspect of the invention may provide a method including using a light source in a sensor housing of an analyte sensor to emit excitation light to an analyte indicator on at least a portion of the sensor housing. The method may include using the analyte indicator to emit an amount of light indicative of an analyte level in a first medium in proximity to the analyte indicator. The method may include using a protective material on at least a portion of the analyte indicator to reduce degradation of the analyte indicator by catalytically decomposing or inactivating one or more in vivo reactive oxygen species or biological oxidizers. The protective material may have a thickness that is thin enough to allow at least some of the excitation light emitted by the light source to pass through the protective material and into an environment surrounding the analyte sensor. The method may include using a signal photodetector in the sensor housing to receive light emitted by the analyte indicator and generate a measurement signal indicative of the amount of light emitted by the analyte indicator and received by the signal photodetector. The method may include using a reference photodetector in the sensor housing to receive light emitted by the light source and reflected by one or more of the analyte indicator and the environment surrounding the analyte sensor and generate a reference signal indicative of an amount of the light received by the reference photodetector. The method may include using a transceiver interface of the analyte sensor to convey sensor measurements including one or more measurements of the measurement signal and one or more measurements of the reference signal. The method may include using a sensor interface of a transceiver to receive the sensor measurements conveyed by the analyte sensor. The method may include using a processor of the transceiver to infer information about a condition of the environment surrounding the analyte sensor and calculate an analyte level in a second medium using at least one or more of the sensor measurements and the inferred information about the condition of the environment surrounding the sensor.

In some embodiments, inferring the information about the condition of the environment surrounding the analyte sensor may include estimating a healing state of tissue surrounding the sensor. In some embodiments, calculating an analyte level in the second medium using at least the one or more of the sensor measurements and the inferred information about the condition of the environment surrounding the sensor may include: adjusting one or more parameters of a conversion function based on at least the inferred information about the condition of the environment surrounding the sensor, and using the adjusted conversion function and the one or more of the sensor measurements to calculate the analyte level in the second medium. In some embodiments, calculating an analyte level in the second medium using at least the one or more of the sensor measurements and the inferred information about the condition of the environment surrounding the sensor may include selecting a conversion function based on at least the inferred information about the condition of the environment surrounding the sensor, and using the selected conversion function and the one or more of the sensor measurements to calculate the analyte level in the second medium.

In some embodiments, the protective material may be sputtered on the analyte indicator. In some embodiments, the protective material may include platinum. In some embodiments, the protective material may have a thickness in a range from 1 nm to 20 nm. In some embodiments, the protective material may have a thickness in a range from 3 nm to 6 nm. In some embodiments, the protective material may have a thickness in a range from 8 nm to 12 nm. In some embodiments, the protective material may have a thickness of 10 nm.

In some embodiments, the environment surrounding the sensor may include one or more of tissue, blood, and clotting. In some embodiments, the light received by the reference photodetector may include light that was emitted by the light source, passed through the analyte indicator, and was reflected by tissue outside the analyte sensor.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
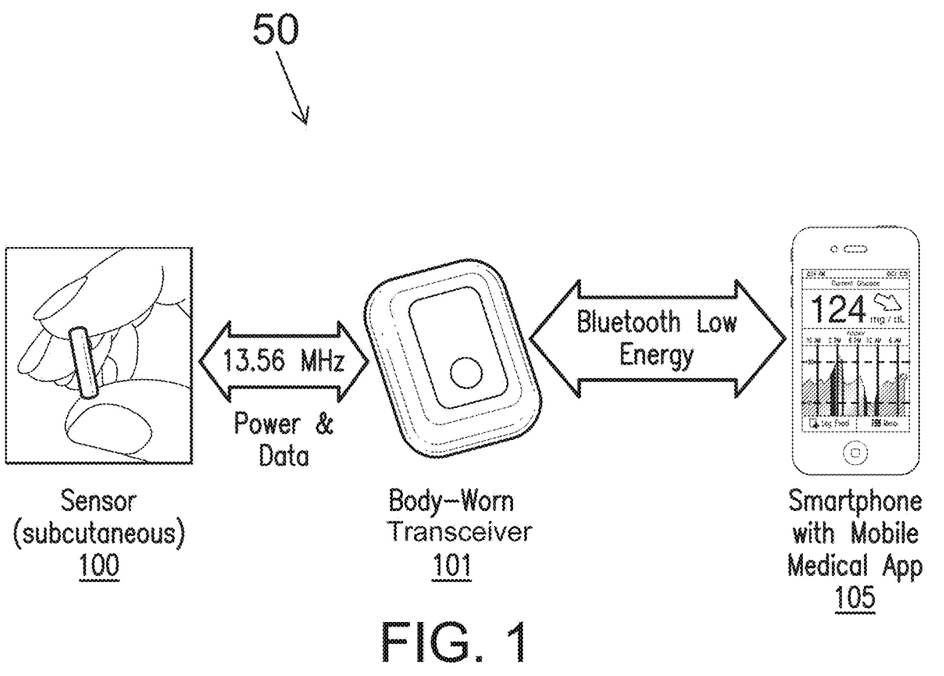
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, and a display device 105. In some embodiments, the sensor 100 may be a small, fully subcutaneously implantable sensor that takes one or more measurements indicative of analyte (e.g., glucose) levels in a first medium (e.g., interstitial fluid) of a living animal (e.g., a living human). However, this is not required, and, in some alternative embodiments, the sensor 100 may be a partially implantable (e.g., transcutaneous) sensor or a fully external sensor.

In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte levels) wirelessly (e.g., via a Bluetooth™ communication standard such as, for example and without limitation Bluetooth Low Energy) to a hand held application running on a display device 105 (e.g., smartphone). In some embodiments, information can be downloaded from the transceiver 101 through a Universal Serial Bus (USB) port. In some embodiments, the analyte monitoring system 50 may include a web interface for plotting and sharing of uploaded data.

Figure 2:
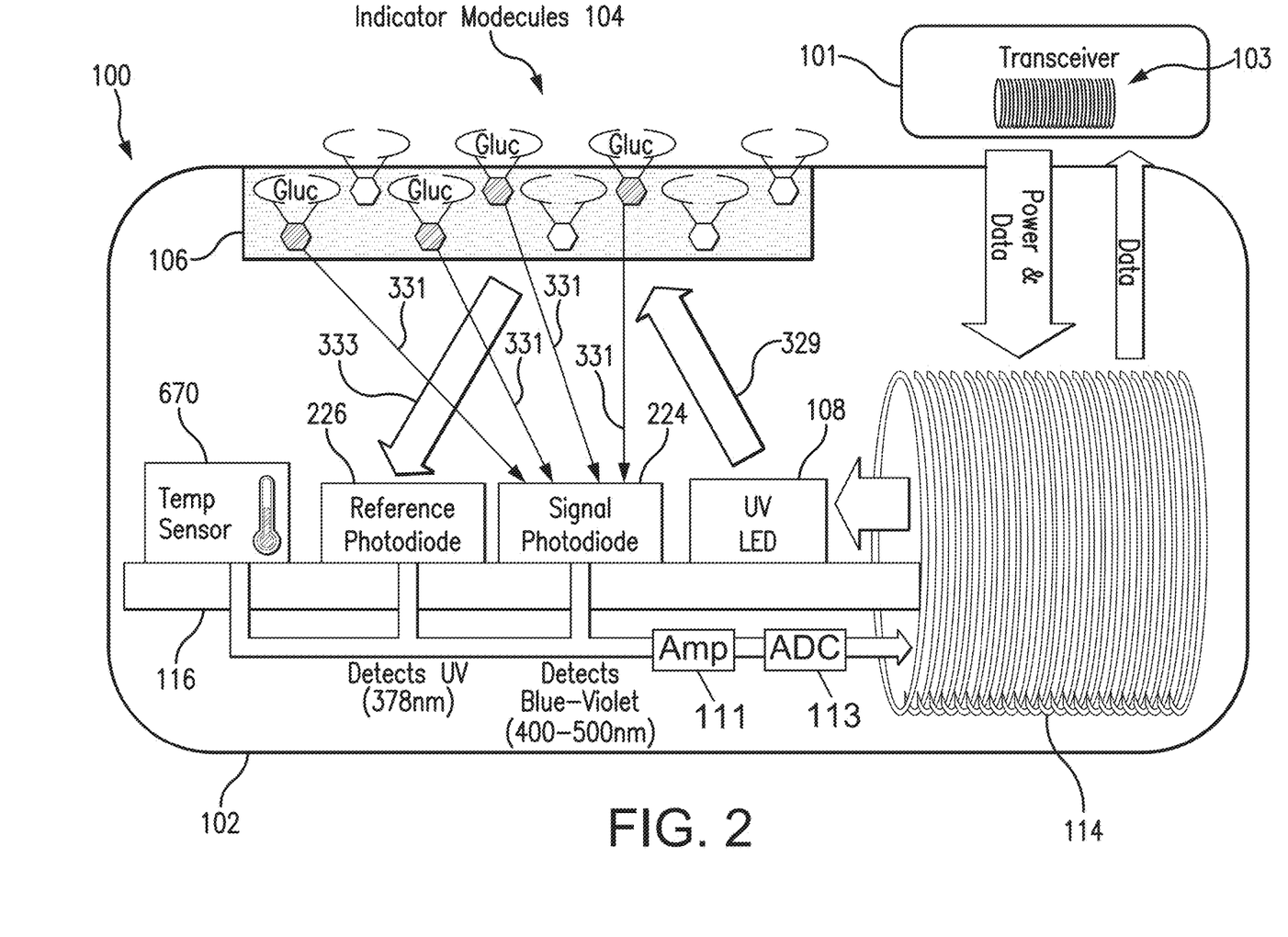
FIG. 2 is a schematic view illustrating a sensor and transceiver of an analyte monitoring system embodying aspects of the present invention.

In some embodiments, as illustrated in FIG. 2, the transceiver 101 may include an inductive element 103, such as, for example, a coil. In some embodiments, the transceiver 101 may generate an electromagnetic wave or electrodynamic field (e.g., by using a coil) to induce a current in an inductive element 114 of the sensor 100. In some non-limiting embodiments, the sensor 100 may use the current induced in the inductive element 114 to power the sensor 100. However, this is not required, and, in some alternative embodiments, the sensor 100 may be powered by an internal power source (e.g., a battery).

In some embodiments, the transceiver 101 may convey data (e.g., commands) to the sensor 100. For example, in some non-limiting embodiments, the transceiver 101 may convey data by modulating the electromagnetic wave generated by the inductive element 103 (e.g., by modulating the current flowing through the inductive element 103 of the transceiver 101). In some embodiments, the sensor 100 may detect/extract the modulation in the electromagnetic wave generated by the transceiver 101. Moreover, the transceiver 101 may receive data (e.g., one or more sensor measurements) from the sensor 100. For example, in some non-limiting embodiments, the transceiver 101 may receive data by detecting modulations in the electromagnetic wave generated by the sensor 100, e.g., by detecting modulations in the current flowing through the inductive element 103 of the transceiver 101.

In some non-limiting embodiments, as illustrated in FIG. 2, the sensor 100 may be include a sensor housing 102 (i.e., body, shell, capsule, or encasement), which may be rigid and biocompatible. The sensor 100 may include an analyte indicator 106, such as, for example, a polymer graft coated, diffused, adhered, or embedded on or in at least a portion of the exterior surface of the sensor housing 102. The analyte indicator 106 (e.g., polymer graft) of the sensor 100 may include indicator molecules 104 (e.g., fluorescent indicator molecules) exhibiting one or more detectable properties (e.g., optical properties) based on the level, amount, or concentration of the analyte in proximity to the analyte indicator 106.

In some embodiments, as shown in FIG. 2, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from one or more of the analyte indicator 106 and environment (e.g., tissue) surrounding the sensor 100 as reflection light 333. In some non-limiting embodiments, one or more of the photodetectors may be covered by one or more filters (e.g., one or more bandpass filters) that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670.

In some embodiments, as illustrated in FIG. 2, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116 and/or a core (e.g., ferrite core) for the inductive element 114. In some embodiments, the semiconductor substrate 116 and/or a core may provide communication paths between the various secured components.

In some embodiments, the one or more of the sensor housing 102, analyte indicator 106, indicator molecules 104, light source 108, photodetectors 224, 226, temperature transducer 670, substrate 116, and inductive element 114 of sensor 100 may include some or all of the features described in one or more of U.S. patent application Ser. No. 13/761,839, filed on Feb. 7, 2013, U.S. patent application Ser. No. 13/937,871, filed on Jul. 9, 2013, and U.S. patent application Ser. No. 13/650,016, filed on Oct. 11, 2012, all of which are incorporated by reference in their entireties. Similarly, the structure and/or function of the sensor 100 and/or transceiver 101 may be as described in one or more of U.S. patent application Ser. Nos. 13/761,839, 13/937,871, and 13/650,016.

Although in some embodiments, as illustrated in FIG. 2, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required. In some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface device. In some embodiments where the sensor 100 includes an antenna (e.g., inductive element 114), the transceiver interface device may include the antenna (e.g., inductive element 114) of sensor 100. In some of the transcutaneous embodiments where there exists a wired connection between the sensor 100 and the transceiver 101, the transceiver interface device may include the wired connection.

In some embodiments, the sensor 100 may include a protective material that protects the analyte indicator 106 of the sensor 100 from the effects of reactive oxygen species (ROS)-driven oxidation. In some embodiments, the protective material may include a metal that catalyzes the breakdown of ROS before the ROS can react with indicator molecules 104 of the analyte indicator 106. In some embodiments, the metal of the protective material may include one or more of copper, tungsten, platinum, iron, molybdenum, cobalt, silver, palladium, manganese, and oxides, alloys, and complexes of those elements. In some embodiments, the protective material may be in the form of a coating sputter-deposited on at least a part of the sensor 100. In some non-limiting embodiments, the thickness of the protective material may be within a range from 0.5 nm to 2.5 mm, within a range from 1 nm to 20 nm, within a range from 8 nm to 12 nm, or within a range from 3 nm to 6 nm, and these ranges should be understood as describing and disclosing all range values (including all decimal or fractional minimum range values) and sub-ranges within these ranges. In some non-limiting embodiments, the protective material may have a thickness of, for example and without limitation, 10 nm.

In some embodiments, the protective material may be applied to the analyte indicator 106 using sputter coating techniques. For example, the techniques can use sputtering targets comprising copper, tungsten, platinum, iron, molybdenum, cobalt, silver, palladium, manganese, and oxides, alloys, and complexes of those elements. In some embodiments, the analyte indicator 106 that has been sputter coated with metal or metal oxide may remain sufficiently porous to allow analytes to pass through the sputter coating and into the analyte indicator 106 but still work effectively as a protective barrier against the diffusion of hydrogen peroxide into the analyte indicator 106. In some embodiments, the metal or metal oxide acting as a catalyst may be configured as a slightly tortuous diffusion layer between outside world and inner graft, which protects the indicator from hydrogen peroxide even at high concentrations and fast physiological production rates. The slightly tortuous diffusion layer may also be characterized as a permanently selective catalytic barrier.

Sputter deposition is a well-known method of depositing thin metal films by sputtering, i.e. ejecting, material from a metal source or "target," after which the atoms from the target deposit onto a substrate. Typically, within a vacuum sealed environment, high energy ionized gases form a plasma and are projected at a target which causes atoms of the metal target to be broken off from the target. As the metal atoms dislodged from the target deposit onto a substrate, a thin film of that metal forms on and bonds to the substrate. Depending on the gas used for projection onto the target and the composition of the target itself, the metal film that is deposited on to the substrate may be a pure metal, an alloy, an oxide, a nitride, an oxynitride, etc.

Figure 3A:
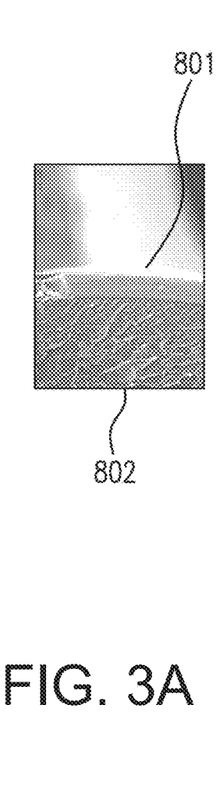
FIGS. 3A, 3B, and 3C are cross-sectional scanning electron microscope (SEM) images, at increasing magnification levels, of metallic gold sputtered onto a sensor.
Figure 3B:
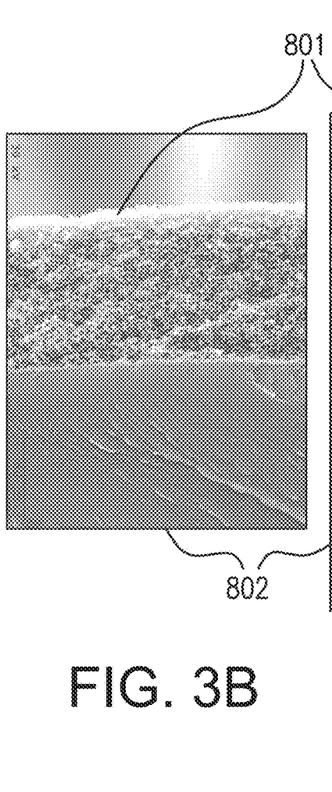
Figure 3C:
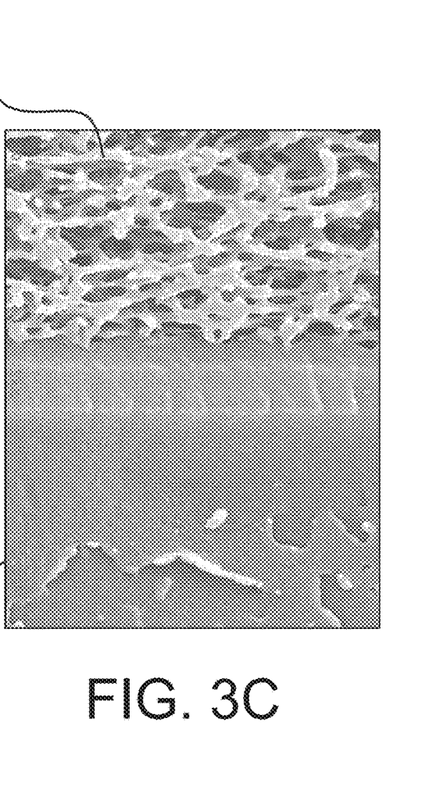

FIGS. 3A-3C are three SEM images, increasing in magnification, of the analyte indicator 106 sputter coated with a protective material. In the images shown in FIGS. 3A-3C, the protective material is gold. By itself, the porous analyte indicator 106 may not be visible by SEM. The images in the photos are of metallic gold, which is visible under SEM, sputtered onto the surface of an analyte indicator 106 in an embodiment where the analyte indicator 106 is a hydroxyethylmethacrylate (HEMA) copolymer graft 801. Thus, these photos are only of the metallic gold shell covering the surface of the analyte-indicating graft 801 following sputter deposition using a gold target. The graft 801 used for FIGS. 3A-3C was cleaved and then sputtered, such that the cross-sectional image and full depth of the graft membrane could be observed under SEM. If sputtered from outside only, then cleaved, then SEM imaged, the expected image would be a metallic porous thin layer riding atop an invisible organic graft layer below. In some embodiments, the metallic gold layer visible in the graft region may be very thin (e.g., a few nanometers) and may have a high surface area (e.g., a surface area that at least matches the surface area of the porous analyte indicator 106, which may be the porous graft 801). Sputter coating the graft 801 with metal does not clog or foul the macro-porosity of the graft 801; i.e. analytes of interest will still be able to diffuse through and interact with indicator molecules 104. In some embodiments, the protective material used to protect the sensor 100 may cover, surround, or encapsulate the sensor housing 102 (e.g., sensor body 802) and analyte indicator 106 (e.g., graft 801) completely. In some alternative embodiments, the protective material may cover the analyte indicator 106 (e.g., graft 801) completely and only a portion of the sensor housing 102 (e.g., sensor body 802) and still protect the indicator region of the sensor 100. In some other alternative embodiments, the protective material may only cover a portion of the analyte indicator 106 (e.g., graft 801) and/or only a portion of the sensor housing 102 (e.g., sensor body 802) and still protect the indicator region of the sensor 100.

Figure 4:
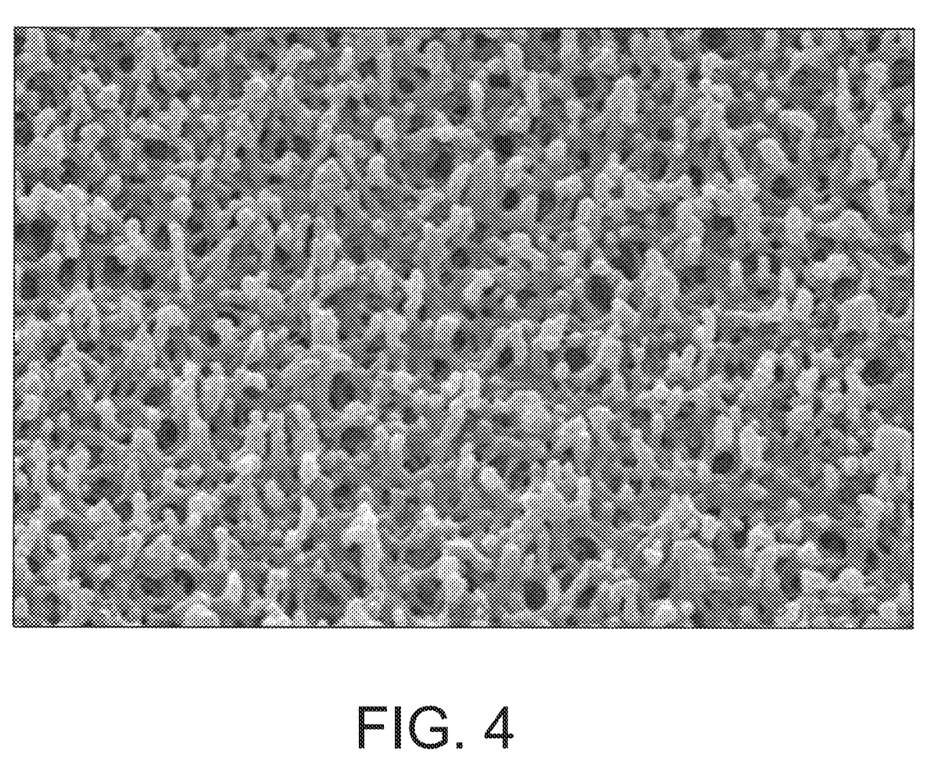
FIG. 4 is a SEM image of the outside surface of a sensor sputtered with gold.

FIG. 4 is an SEM photo from the outside surface of the analyte indicator 106 (e.g., graft 801) looking inward toward the sensor housing 102 (e.g., sensor body 802) according to one non-limiting embodiment. Again, this image is not technically of the graft, but is rather an image of metallic gold sputtered over the graft, which allows the graft to be visualized by SEM. This image shows an embodiment in which the entire surface area of the analyte indicator 106 (e.g., graft 801) is effectively coated with the protective material. Thus, in this embodiment, it can be inferred that the surface area of exposed protective is at least equivalent to the surface area of the analyte indicator 106.

Figure 5A:
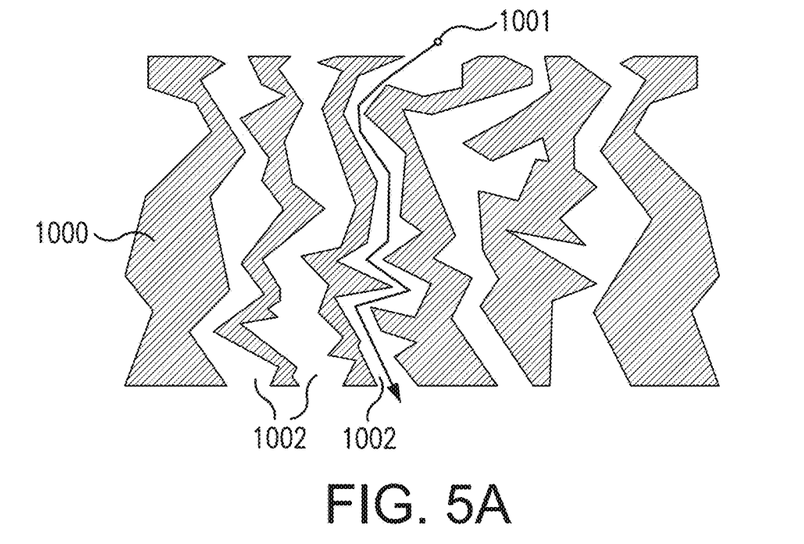
FIGS. 5A and 5B are diagrams of tortuous membranes of porous sensor grafts in accordance with embodiment of the present invention.

In some non-limiting embodiments, the analyte indicator 106, which may cover a portion of or the entire sensor housing 102, may have a tortuous membrane structure. FIG. 5A is a representation of a tortuous membrane structure 1000 of the analyte indicator 106 according to some non-limiting embodiments of the invention. In some embodiments, a solute 1001 would have to follow a tortuous diffusion path 1002 to pass through and cross the membrane 1000.

Figure 5B:
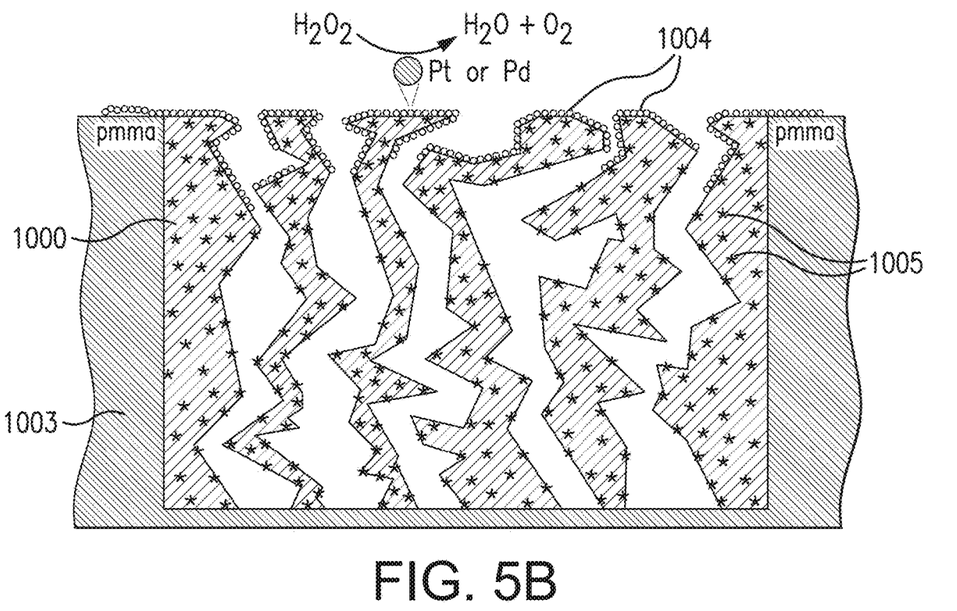

In some non-limiting embodiments, as shown in FIG. 5B, the tortuous membrane 1000 may have a metalized surface layer 1004 and indicator molecules 1005. In some embodiments, the metalized surface layer 1004 may create a tortuous diffusion barrier. However, in some embodiments, the macro-pores of the tortuous membrane 1000 may still be wide open (e.g., about 1 micron wide) and without metal fouling.

In some embodiments, the depth of the sputtered protective material on the tortuous membrane structure 1000 of the porous analyte indicator 106 may be limited to line of sight at the micro level. In some embodiments, metal sputtered from a target generally cannot diffuse deep into the tortuous membrane structure 1000 because the sputtered metal deposits upon impact. Thus, areas below the surface of the tortuous membrane structure 1000 that are shadowed may remain uncoated, as shown in FIG. 5B. In some embodiments, the depth of this metalized layer 1004 into the porous analyte indicator 106 may be 5 microns or less. In some alternative embodiments, additional pressure may be introduced to the sputtering environment, magnetic fields may be used, or other methods may be used to cause the tortuous membrane 1000 to be sputtered past the point of line of sight deposition, such that the metalized layer 1004 may extend further down (or through) the full depth of the porous analyte indicator 106. As noted above, the analyte indicator 106 may remain porous after sputter deposition.

In some other alternative embodiments, the metal applied (e.g., sputtered) on the tortuous membrane structure 1000 of the porous analyte indicator 106 may not be present in the pores of the analyte indicator 106. For example, in some alternative embodiments, the metal may be applied (e.g., sputtered) on the analyte indicator 106 while the analyte indicator 106 is in a dried state. Drying the porous analyte indicator 106 may cause the porous analyte indicator 106 to contract and the pores of the tortuous membrane structure 1000 of the analyte indicator 106 to constrict. In some embodiments, metal sputtered on the dried analyte indicator 106 will not be able to enter the constricted pores of the dried analyte indicator 106. In some embodiments, when the dried analyte indicator 106 is hydrated (e.g., by placing the analyte indicator 106 in a liquid such as, for example, water, a saline solution, or interstitial fluid), the analyte indicator 106 may expand, and the metal sputtered on the analyte indicator 106 may crack and/or break apart but remain deposited on the hydrated, porous analyte indicator 106.

Figure 6:
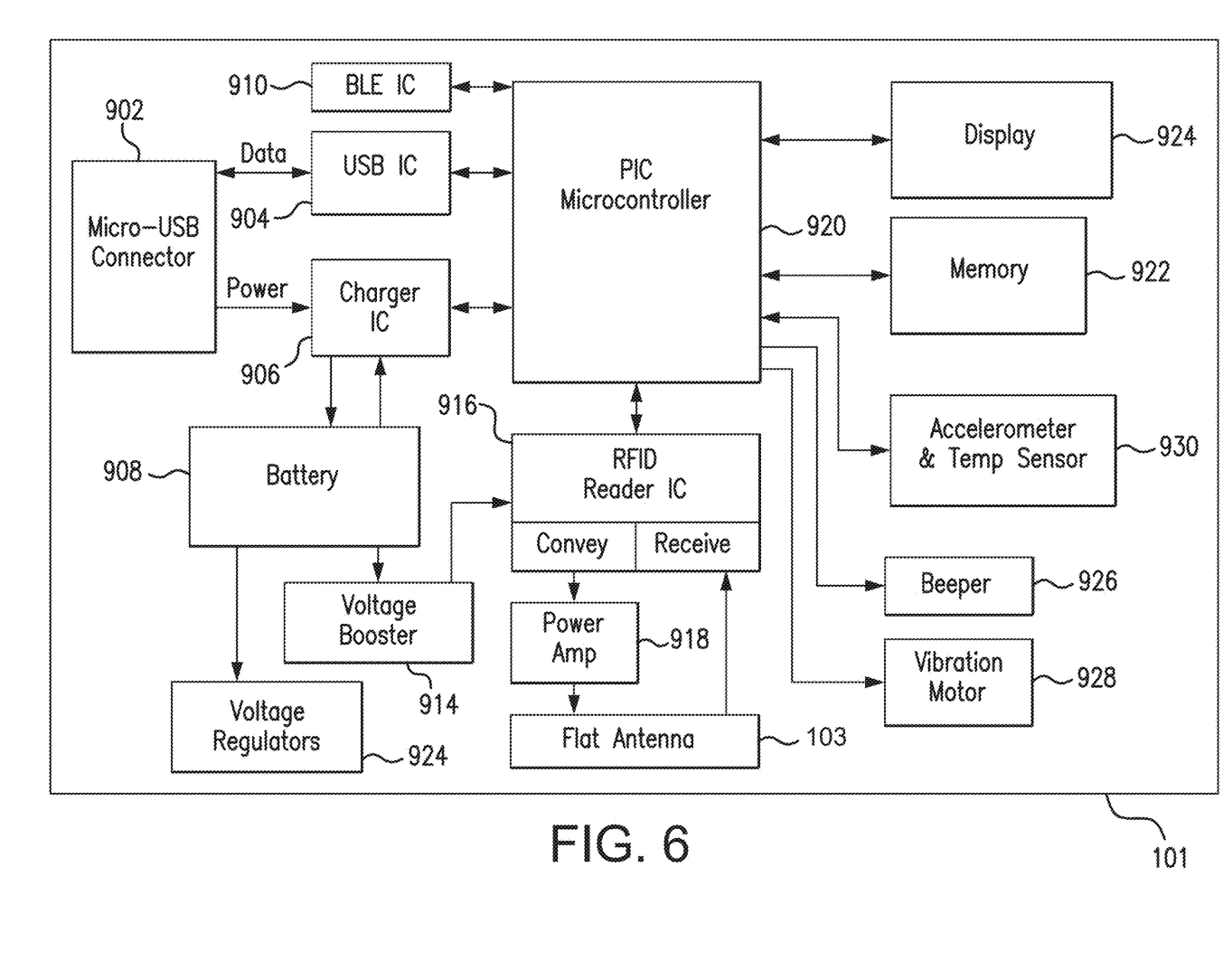
FIG. 6 is a schematic view illustrating a transceiver embodying aspects of the present invention.

FIG. 6 is a schematic view of an external transceiver 101 according to a non-limiting embodiment. In some embodiments, as shown in FIG. 6, the transceiver 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 105 (e.g., a smartphone) and/or to receive power, which may be used, for example, to charge the battery 908.

In some embodiments, as shown in FIG. 6, the transceiver 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, as shown in FIG. 6, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In some embodiments, as illustrated in FIG. 6, the inductive element 103 may be a flat antenna. In some non-limiting embodiments, the antenna may be flexible. However, this is not required, and, in some alternative embodiments, the inductive element 103 may be a non-flat antenna and/or a non-flexible antenna. In some embodiments, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

In some embodiments, as shown in FIG. 6, the transceiver 101 may include a processor 920 and a memory 922 (e.g., Flash memory). In some non-limiting embodiments, the memory 922 may be non-volatile and/or capable of being electronically erased and/or rewritten. In some non-limiting embodiments, the processor 920 may be, for example and without limitation, a peripheral interface controller (PIC) microcontroller. In some embodiments, the processor 920 may control the overall operation of the transceiver 101. For example, the processor 920 may control the connector IC 904 or wireless communication IC 910 to transmit data via wired or wireless communication and/or control the RFID reader IC 916 to convey data via the inductive element 103. The processor 920 may also control processing of data received via one or more of the inductive element 103, connector 902, and wireless communication IC 910.

In some embodiments, the transceiver 101 may include a sensor interface device, which may enable communication by the transceiver 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, as shown in FIG. 6, the transceiver 101 may include a display 924 (e.g., liquid crystal display and/or one or more light emitting diodes), which processor 920 may control to display data (e.g., analyte levels). In some embodiments, the transceiver 101 may include a speaker 926 (e.g., a beeper) and/or a vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or a temperature sensor, that may be used in the processing performed by the processor 920.

In some embodiments, the transceiver 101 may be a body-worn transceiver that is a rechargeable, external device worn over the sensor implantation or insertion site. In some embodiments, the transceiver 101 may be placed using an adhesive patch or a specially designed strap or belt. In some non-limiting embodiments, the transceiver 101 may supply power to the proximate sensor 100. In some non-limiting embodiments, power may be supplied to the sensor 100 through an inductive link (e.g., an inductive link of 13.56 MHz). However, it is not required that the sensor 100 receive power from the transceiver 101 (e.g., in the case of a battery-powered sensor).

In some embodiments, the external transceiver 101 may receive from the analyte sensor 100 one or more sensor measurements indicative of an analyte level in a first medium (e.g., interstitial fluid) in proximity to the analyte indicator 106 of the analyte sensor 100. In some non-limiting embodiments, the one or more sensor measurements may include, for example and without limitation, light and/or temperature measurements (e.g., one or more measurements indicative of the level of emission light 331 from the indicator molecules 104 as measured by the photodetector 224, one or more measurements indicative of the level of reflection light 333 as measured by the photodetector 226, and/or one or more temperature measurements as measured by the temperature transducer 670). In some non-limiting embodiments, the transceiver 101 may receive one or more sensor measurements periodically (e.g., every 1, 2, 5, 10, or 15 minutes). However, this is not required, and, in some alternative embodiments, the transceiver 101 may receive one or more sensor measurements (e.g., by swiping, hovering, or otherwise bringing the transceiver 101 in proximity to the sensor 101).

In some embodiments, the transceiver 101 may calculate a level (e.g., concentration) of the analyte (e.g., glucose) in the first medium (e.g., interstitial fluid) using at least the received one or more sensor measurements. In some embodiments, the transceiver 101 may additionally or alternatively calculate a level of the analyte in a second medium (e.g., blood) using at least the received one or more sensor measurements and/or the calculated first medium analyte level. In some non-limiting embodiments, the transceiver 101 may calculate the second medium analyte level using the following conversion function: $M1\_ROC/p_2 + (1+p_3/p_2) * M1\_analyte$, where $M1\_ROC$ is the rate of change of the first medium analyte level, $p_2$ is analyte diffusion rate, $p_3$ is the analyte consumption rate, and $M1\_analyte$ is the calculated first medium analyte level. In some embodiments, the transceiver 101 may display one or more calculated analyte levels (e.g., one or calculated second medium analyte levels) by displaying the analyte levels on a display of the transceiver 101 or conveying the analyte levels to a display device 105 (see FIG. 1). In some embodiments, the transceiver 101 may calculate one or more analyte level trends. In some embodiments, the transceiver 101 may determine whether an alert and/or alarm condition exists, which may be signaled to the user (e.g., through vibration by vibration motor 928 and/or an LED of the transceiver's display 924 and/or a user interface of a display device 105). In some embodiments, the transceiver 101 may store one or more calculated analyte levels (e.g., in memory 922).

In some embodiments, the transceiver 101 may convey information (e.g., one or more of sensor data, calculated analyte levels, calculated analyte level rates of change, alerts, alarms, and notifications) may be transmitted to a display device 105 (e.g., via Bluetooth Low Energy with Advanced Encryption Standard (AES)-Counter CBC-MAC (CCM) encryption) for display by a mobile medical application (MMA) being executed by the display device 105. In some non-limiting embodiments, the MMA may generate alarms, alerts, and/or notifications (in addition to or as an alternative to receiving alerts, alarms, and/or notifications from the transceiver 101). In one embodiment, the MMA may be configured to provide push notifications.

In some embodiments, the analyte monitoring system 50 may calibrate the conversion of one or more sensor measurements to one or more analyte levels. In some embodiments, the calibration may be performed approximately periodically (e.g., every 12 or 24 hours). In some embodiments, the calibration may be performed using one or more reference measurements (e.g., one or more self-monitoring blood glucose (SMBG) measurements), which may be entered into the analyte monitoring system 50 using the user interface of the display device 105. In some embodiments, the transceiver 101 may receive the one or more reference measurements from the display device 105 and perform the calibration using the one or more reference measurements as calibration points.

Figure 7:
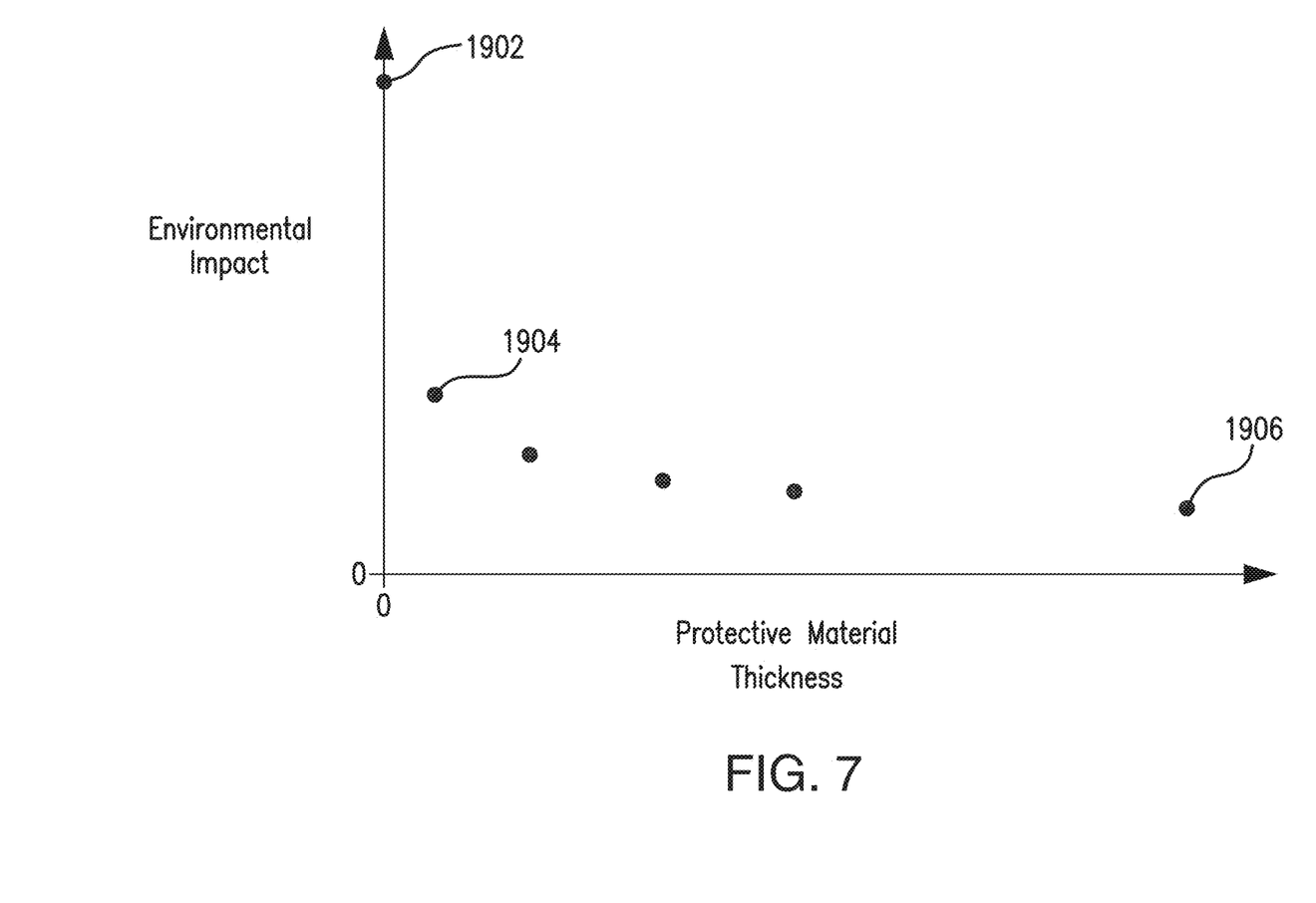
FIG. 7 depicts an exemplary relationship between a thickness of the protective material applied to an analyte indicator of a sensor and the impact that the environment outside the sensor has on signal(s) output by one or more photodetectors of the sensor.

FIG. 7 depicts an exemplary relationship between a thickness of the protective material applied to (e.g., coated on) the analyte indicator 106 on at least a portion of the housing 102 of the sensor 100 and the impact that the environment outside the sensor 100 has on the signal(s) output by one or more photodetectors (e.g., one or more of photodetectors 224 and 226) of the sensor 100. The environment outside the sensor 100 may include, for example and without limitation, the tissue surrounding the sensor 100 and/or external light (e.g., ambient light). As shown in FIG. 7, the impact that the environment outside the sensor 100 has on the signal(s) output by one or more photodetectors of the sensor 100 may decrease as the thickness of the protective material increases. For example, at point 1902, there is no protective material applied to the analyte indicator 106, and the impact of the environment outside the sensor 100 is the greatest because there is clear visibility to the surrounding environment (e.g., tissue, blood, clotting). In contrast, at point 1906, the protective material is at its thickest, which results in high light reflection (e.g., high reflection of the excitation light 329 as reflection light 333 (see FIG. 2)), and the impact of the environment outside the sensor 100 is at its lowest because there is minimal visibility to the surrounding environment. At point 1904, a thin layer of protective material is present on the analyte indicator 106, but the protective material is thin enough to allow visibility to the surrounding environment (e.g., tissue, blood, clotting), and the environment outside the sensor 100 has a significant impact on the signal(s) output by one or more photodetectors of the sensor 100.

Figure 8:
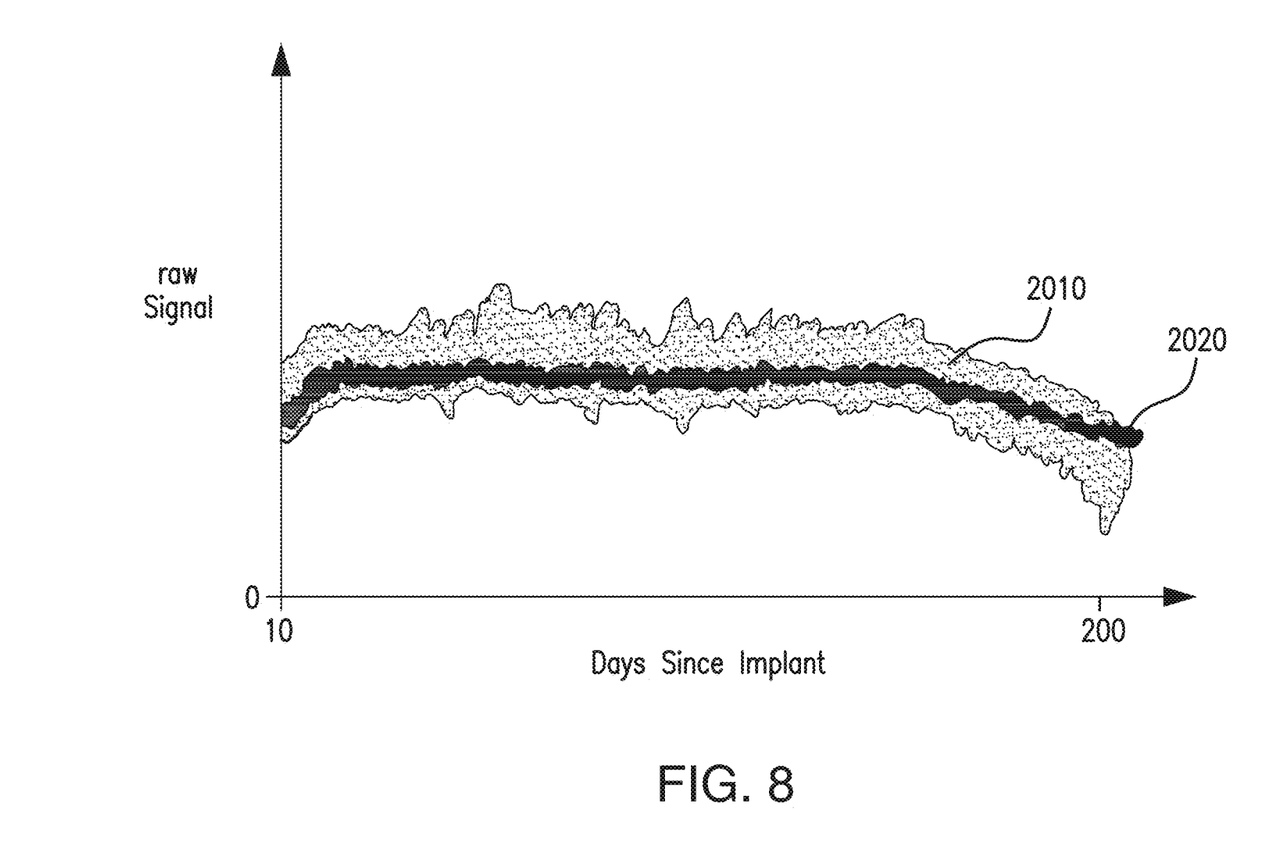
FIG. 8 illustrates an exemplary relationship between signals output by photodetectors of an analyte sensor having visibility to the environment surrounding the sensor and days elapsed after initial implantation or insertion of the sensor within a patient's tissue.

FIG. 8 illustrates an exemplary relationship between signals 2010 and 2020 output by photodetectors of the sensor 100 having visibility to the environment surrounding the sensor 100 and days elapsed after initial implantation or insertion of the sensor 100 within a patient's tissue. In some embodiments, the signal 2010 may be an analyte measurement signal output by the photodetector 224. In some embodiments, the signal 2010 may be indicative of the amount of light 331 emitted by indicator molecules 104 of the analyte indicator 106, which may be indicative of the amount of analyte in a first medium in proximity to the analyte indicator 106. In some embodiments, the signal 2020 may be a reference signal output by the photodetector 226. In some embodiments, the signal 2020 may be indicative of the amount of reflection light 333. In some embodiments, the reflection light 333 may be excitation light 329 that has been reflected by one or more of the analyte indicator 106 and the environment (e.g., tissue, blood, clotting) surrounding the sensor 100. As shown in FIG. 8, one or more of the signals 2010 and 2020 may one or more of increases, decreases, and plateaus. In some embodiments, one or more of the increases, decreases, and plateaus may be associated with the wound healing process in the tissue surrounding the sensor after the trauma of the sensor implantation. In some embodiments, visibility to the environment surrounding the sensor 100 may enable insight to the wound healing process in the tissue surrounding the sensor 100. As shown in FIG. 8, the analyte measurement signal 2010 may decline (e.g., gradually decline) as the time after implantation increases. In some embodiments, decline in the analyte measurement signal 2010 may be associated with degradation of the indicator molecules 104 of the analyte indicator 106. In some embodiments, visibility to the environment outside of the sensor 100 may enable ratiometric processing of the sensor measurements.

In some embodiments, the protective material applied (e.g., sputtered) on at least a portion of the analyte indicator 106 may have a thickness selected to be both (i) thick enough to reduce degradation of the analyte indicator 106 (e.g., by providing catalytic decomposition of reactive oxygen species or biological oxidizers) and (ii) thin enough to allow visibility of the environment outside the sensor 100. In some embodiments, a protective material thick enough to reduce degradation of the analyte indicator 106 may produce of useful life of 90 days or more while implanted within a human body. In some embodiments, a protective material thick enough to reduce degradation of the analyte indicator 106 may produce of useful life of 180 days or more while implanted within a human body. In some embodiments, a protective material thin enough to allow visibility of the environment outside the sensor 100 may allow light to pass through the protective material. In some embodiments, a protective material thin enough to allow visibility of the environment outside the sensor 100 if the environment outside the sensor 100 able to impact one or more signals output by one or more photodetectors of the sensor 100. In some non-limiting embodiments, a protective material that is both thick enough to reduce degradation of the analyte indicator 106 and (ii) thin enough to allow visibility of the environment outside the sensor 100 may have a thickness of, for example and without limitation, 10 nm. In some non-limiting embodiments, a protective material that is both thick enough to reduce degradation of the analyte indicator 106 and (ii) thin enough to allow visibility of the environment outside the sensor 100 may have a thickness within a range of, for example and without limitation, 3 nm to 6 nm.

In some embodiments, the transceiver 101 may receive from the sensor 100 one or more sensor measurements. In some embodiments, the received sensor measurements may include one or more of measurements may be indicative of an analyte level in the first medium (e.g., interstitial fluid). In some non-limiting embodiments, the one or more sensor measurements indicative of the analyte level in the first medium may include one or more measurements of the analyte measurement signal 2010, which may be output by the photodetector 224 in accordance with an amount of light 331 emitted by the indicator molecules 104 of the analyte indicator 106. In some embodiments, the received sensor measurements may additionally or alternatively include one or more of measurements indicative of the environment (e.g., tissue, blood, clotting) surrounding the sensor 100. In some non-limiting embodiments, the one or more sensor measurements indicative of the environment surrounding the sensor 100 may include one or more measurements of the reference signal 2020, which may be output by the photodetector 226 in accordance with the amount of reflection light 333. In some embodiments, the reflection light 333 may be excitation light 329 that has been reflected by one or more of the analyte indicator 106 and the environment (e.g., tissue, blood, clotting) surrounding the sensor 100.

In some embodiments, the transceiver 101 (e.g., the processor 920 of transceiver 101) may use the one or more sensor measurements indicative of the environment surrounding the sensor 100 to infer information about a condition of the environment surrounding the sensor 100. In some non-limiting embodiments, the transceiver 101 may use the one or more sensor measurements indicative of the environment surrounding the sensor 100 to estimate the healing state of the tissue surrounding the sensor 100. In some non-limiting embodiments, the transceiver 101 may estimate the healing state of the tissue surrounding the sensor 100 by, for example and without limitation, determining whether one or more of the signals 2010 and 2020 has increased, decreased, or plateaued during different time periods.

In some non-limiting embodiments, the transceiver 101 may use the estimated healing state of the tissue surrounding the sensor 100 to adjust how the transceiver 101 calculates an analyte level in the second medium (e.g., blood). For example, in some non-limiting embodiments, the transceiver 101 may adjust one or more parameters of the conversion function (e.g., the analyte diffusion rate) based on at least the estimated healing state of the tissue surrounding the sensor 100 and use the adjusted conversion function and the one or more received sensor measurements indicative of a first medium analyte level to calculate a second medium analyte level. In some non-limiting alternative embodiments, the transceiver 101 may select one of a plurality of conversion functions based on the estimated healing state of the tissue surrounding the sensor 100 and use the selected conversion function and the one or more received sensor measurements indicative of a first medium analyte level to calculate the second medium analyte level.

Figure 9:
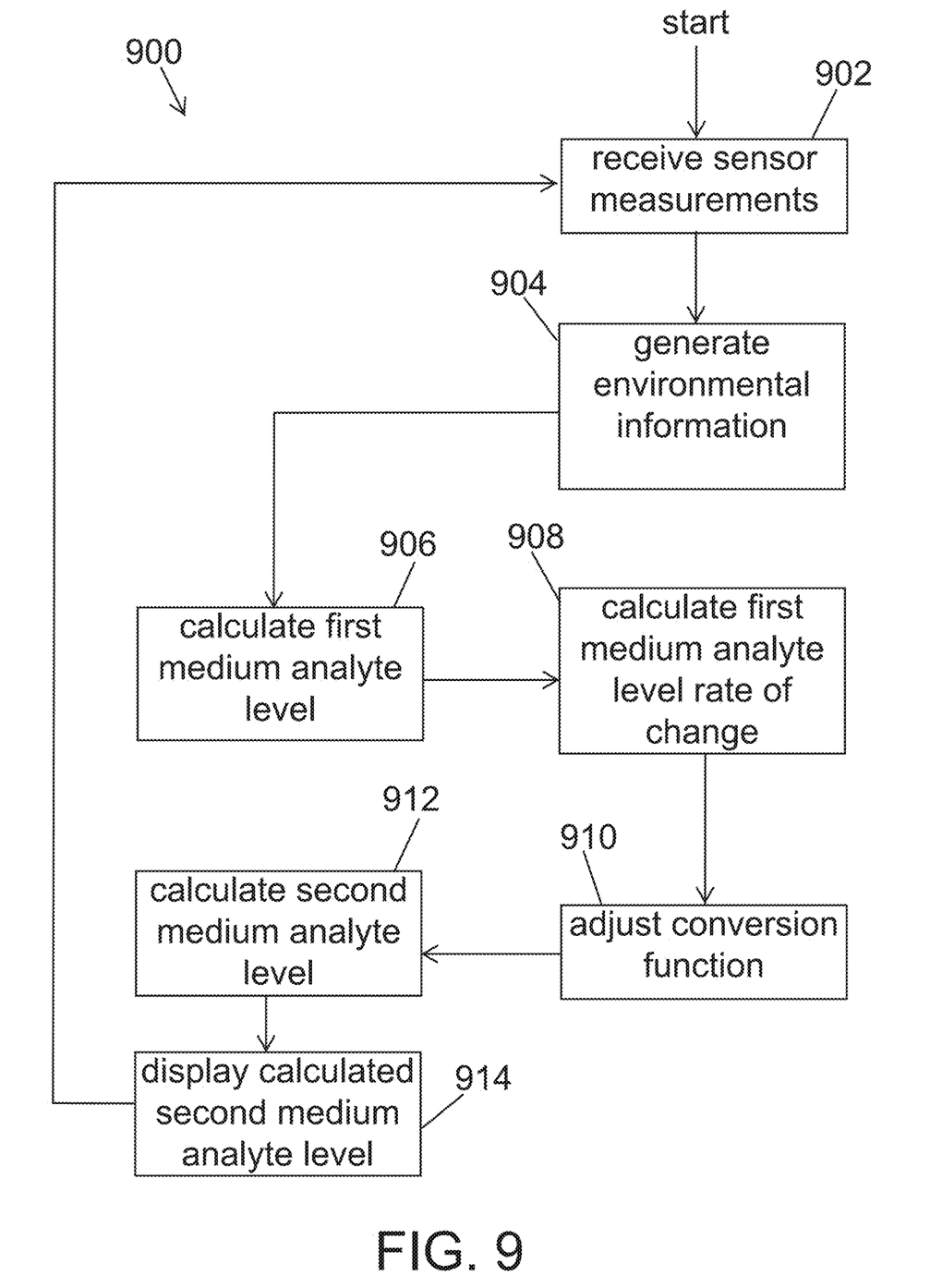
FIG. 9 is a flow chart illustrating an analyte level calculation process embodying aspects of the present invention.

FIG. 9 is a flow chart illustrating a process 900 for calculating second medium analyte levels (e.g., blood analyte levels) according. In some embodiments, one or more steps of the process 900 may be performed by an analyte monitoring system, such as, for example, the analyte monitoring system 50. In some embodiments, one or more steps of the process 900 may be performed by a transceiver, such as, for example, the transceiver 101. In some non-limiting embodiments, one or more steps of the process 900 may be performed by a processor, such as, for example, the processor 920 of the transceiver 101.

In some embodiments, the process 900 may include a step 902 in which the transceiver 101 receives sensor measurements from the sensor 100. In some non-limiting embodiments, the sensor measurements may include, for example and without limitation, one or more light measurements and/or one or more temperature measurements. In some embodiments, the transceiver 101 may receive the sensor measurements after conveying a command (e.g., a measurement command or a read sensor data command) to the sensor 100. However, this is not required, and, in some alternative embodiments, the sensor 100 may control when sensor measurements are conveyed to the transceiver 101, or the sensor 100 may continuously convey sensor measurements to the transceiver 101. In some non-limiting embodiments, the transceiver 101 may receive sensor measurements periodically (e.g., every 1, 2, 5, 10, or 15 minutes).

In some embodiments, the sensor measurements may be associated with a time stamp. In some non-limiting embodiments, the transceiver 101 may receive the time stamp from the sensor 100. In some non-limiting embodiments, the received sensor measurements may include the time stamp.

In some embodiments, the time stamp may reflect the time at which the sensor measurements were taken. However, it is not required that the transceiver 101 receive the time stamp from the sensor 100. For example, in some alternative embodiments, the transceiver 101 may assign the time stamp to the sensor measurements after receiving the one or more sensor measurements. In these embodiments, the time stamp may reflect when the transceiver 101 received the sensor measurements.

In some embodiments, the process 900 may include a step 904 in which the transceiver 101 generates information about a condition of the environment surrounding the sensor 100 (e.g., an estimation of the healing state of the tissue surrounding the sensor 100). In some non-limiting embodiments, the received sensor measurements may include one or more sensor measurements indicative of the environment surrounding the sensor 100, and the transceiver 101 may use the one or more sensor measurements indicative of the environment surrounding the sensor 100 to generate the information about the condition of the environment surrounding the sensor 100.

In some embodiments, the process 900 may include a step 906 in which the transceiver 101 calculates first medium analyte level (e.g., an ISF analyte level) using one or more of the sensor measurements received from the sensor 100. In some embodiments, the received sensor measurements may include one or more measurements indicative of an analyte level in the first medium (e.g., interstitial fluid), and the transceiver 101 may use the one or more measurements indicative of an analyte level in the first medium to calculate the first medium analyte level. In some embodiments, the first medium analyte level may be a measurement of the amount or concentration of the analyte in the first medium (e.g., interstitial fluid) in proximity to the analyte sensor 100. In some non-limiting embodiments, calculation of the first medium analyte level may include, for example and without limitation, some or all of the features described in U.S. application Ser. No. 13/937,871, filed on Jul. 9, 2013, now U.S. Pat. No. 9,414,775, which is incorporated by reference herein in its entirety.

In some embodiments, the process 900 may include a step 908 in which the transceiver 101 calculates a first medium analyte level rate of change ("M1_ROC"). In some embodiments, the transceiver 101 may calculate the M1_ROC using at least the first medium analyte level calculated in step 906 and one or more previously calculated first medium analyte levels (e.g., one or more first medium analyte levels calculated using previously received sensor measurements).

In some embodiments, the process 900 may include a step 910 in which the transceiver 101 adjusts a conversion function used to calculate a second medium analyte level (e.g., a blood analyte level) based on the generated information about the condition of the environment surrounding the sensor 100. In some non-limiting embodiments, the transceiver 101 may adjust the conversion function by adjusting one or more parameters (e.g., one or more of the analyte diffusion rate and analyte consumption rate parameters) of the conversion function. In some alternative embodiments, in step 910, the transceiver 101 may select one of a plurality of conversion functions based on the generated information about the condition of the environment surrounding the sensor 100 (e.g., the estimation of the healing state of the tissue surrounding the sensor 100). For instance, in one non-limiting embodiment, the transceiver 101 may use a first conversion function during the initial wound healing process following the initial trauma of the sensor implantation and a second conversion after the initial wound healing process has completed (e.g., as indicated by an increase and/or plateau in one or more of the signals 2010 and 2020).

In some embodiments, the process 900 may include a step 912 in which the transceiver 101 calculates a second medium analyte level (e.g., a blood analyte level). In some embodiments, the transceiver 101 may calculate the second medium analyte level by performing a lag compensation. In some embodiments, the transceiver 101 may calculate the second medium analyte level using at least the first medium analyte level and the M1_ROC calculated in steps 906 and 908, respectively. In some embodiments, the transceiver 101 may calculate the second medium analyte level using a conversion function. In some non-limiting embodiments, the conversion function used in step 912 may have been adjusted (or selected) in step 910.

In some non-limiting embodiments, the process 900 may include a step 914 of displaying the calculated second medium analyte level. In some embodiments, the step 914 may include displaying the calculated second medium analyte level on a display of the transceiver 101. In some embodiments, the step 914 may additionally or alternatively include the transceiver 101 conveying the calculated second medium analyte level to a display device (e.g., display device 105) for display. In some non-limiting embodiments, the transceiver 101 may convey the calculated second medium analyte level to the display device 105 via wired or wireless communication using the display interface of the transceiver 101. In some embodiments, the display device 105 may be configured to receive and display the conveyed second medium analyte level.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. An analyte monitoring system comprising:
  an analyte sensor comprising: (i) a sensor housing, (ii) an analyte indicator on at least a portion of the sensor housing and configured to emit an amount of light indicative of an analyte level in a first medium in proximity to the analyte indicator, (iii) a protective material on at least a portion of the analyte indicator and configured to reduce degradation of the analyte indicator by catalytically decomposing or inactivating one or more in vivo reactive oxygen species or biological oxidizers, (iv) a light source in the sensor housing and configured to emit excitation light to the analyte indicator, (v) a signal photodetector in the sensor housing and configured to receive the amount of light emitted by the analyte indicator and generate a measurement signal indicative of the amount of light emitted by the analyte indicator and received by the signal photodetector, (vi) a reference photodetector in the sensor housing and configured to generate a reference signal indicative of an amount of the excitation light received by the reference photodetector, and (vii) a transceiver interface configured to convey sensor measurements including one or more measurements of the measurement signal and one or more measurements of the reference signal; and
  a transceiver comprising: (i) a sensor interface configured to receive the sensor measurements conveyed by the analyte sensor and (ii) a processor configured to infer information about a condition of the environment surrounding the analyte sensor using at least one or more of the sensor measurements and to calculate an analyte level in a second medium using at least one or more of the sensor measurements and the inferred information about the condition of the environment surrounding the analyte sensor;
  wherein the excitation light received by the reference photodetector includes light that was emitted by the light source, passed through the analyte indicator and the protective material, and was reflected by the environment surrounding the analyte sensor;
  wherein the environment surrounding the analyte sensor includes one or more of tissue, blood, and clotting.

2. The analyte monitoring system of claim 1, wherein said inferring the information about the condition of the environment surrounding the analyte sensor comprises estimating a state of a wound healing process in tissue surrounding the analyte sensor.

3. The analyte monitoring system of claim 1, wherein said calculating the analyte level in the second medium using at least the one or more of the sensor measurements and the inferred information about the condition of the environment surrounding the analyte sensor comprises:
  adjusting one or more parameters of a conversion function based on at least the inferred information about the condition of the environment surrounding the analyte sensor; and
  using the adjusted conversion function and the one or more of the sensor measurements to calculate the analyte level in the second medium.

4. The analyte monitoring system of claim 3, wherein said adjusting one or more parameters of the conversion function comprises adjusting an analyte diffusion rate parameter and/or an analyte consumption rate parameter.

5. The analyte monitoring system of claim 1, wherein said calculating the analyte level in the second medium using at least the one or more of the sensor measurements and the inferred information about the condition of the environment surrounding the analyte sensor comprises:
  selecting a conversion function based on at least the inferred information about the condition of the environment surrounding the analyte sensor; and
  using the selected conversion function and the one or more of the sensor measurements to calculate the analyte level in the second medium.

6. The analyte monitoring system of claim 1, wherein the protective material is sputtered on the analyte indicator.

7. The analyte monitoring system of claim 1, wherein the protective material comprises platinum.

8. The analyte monitoring system of claim 1, wherein the protective material has a thickness in a range from 1 nm to 20 nm.

9. The analyte monitoring system of claim 1, wherein the protective material has a thickness in a range from 3 nm to 6 nm.

10. The analyte monitoring system of claim 1, wherein the protective material has a thickness in a range from 8 nm to 12 nm.

11. The analyte monitoring system of claim 10, wherein the protective material has a thickness of 10 nm.

12. A method comprising:
  using a light source in a sensor housing of an analyte sensor to emit excitation light to an analyte indicator on at least a portion of the sensor housing;

using the analyte indicator to emit an amount of light indicative of an analyte level in a first medium in proximity to the analyte indicator;

using a protective material on at least a portion of the analyte indicator to reduce degradation of the analyte indicator by catalytically decomposing or inactivating one or more in vivo reactive oxygen species or biological oxidizers;

using a signal photodetector in the sensor housing to receive the amount of light emitted by the analyte indicator and generate a measurement signal indicative of the amount of light emitted by the analyte indicator and received by the signal photodetector;

using a reference photodetector in the sensor housing to generate a reference signal indicative of an amount of the excitation light received by the reference photodetector, wherein the excitation light received by the reference photodetector includes light that was emitted by the light source, passed through the analyte indicator and the protective material, and was reflected by the environment surrounding the analyte sensor, and the environment surrounding the analyte sensor includes one or more of tissue, blood, and clotting;

using a transceiver interface of the analyte sensor to convey sensor measurements including one or more measurements of the measurement signal and one or more measurements of the reference signal;

using a sensor interface of a transceiver to receive the sensor measurements conveyed by the analyte sensor; and using a processor of the transceiver to infer information about a condition of the environment surrounding the analyte sensor using at least one or more of the sensor measurements and to calculate an analyte level in a second medium using at least one or more of the sensor measurements and the inferred information about the condition of the environment surrounding the analyte sensor.

13. The method of claim 12, wherein said inferring the information about the condition of the environment surrounding the analyte sensor comprises estimating a state of a wound healing process in tissue surrounding the analyte sensor.

14. The method of claim 12, wherein said calculating the analyte level in the second medium using at least the one or more of the sensor measurements and the inferred information about the condition of the environment surrounding the analyte sensor comprises:

adjusting one or more parameters of a conversion function based on at least the inferred information about the condition of the environment surrounding the analyte sensor; and using the adjusted conversion function and the one or more of the sensor measurements to calculate the analyte level in the second medium.

15. The method of claim 14, wherein said adjusting one or more parameters of the conversion function comprises adjusting an analyte diffusion rate parameter and/or an analyte consumption rate parameter.

16. The method of claim 12, wherein said calculating the analyte level in the second medium using at least the one or more of the sensor measurements and the inferred information about the condition of the environment surrounding the analyte sensor comprises:

selecting a conversion function based on at least the inferred information about the condition of the environment surrounding the analyte sensor; and using the selected conversion function and the one or more of the sensor measurements to calculate the analyte level in the second medium.

17. The method of claim 12, wherein the protective material is sputtered on the analyte indicator.

18. The method of claim 12, wherein the protective material comprises platinum.

19. The method of claim 12, wherein the protective material has a thickness in a range from 1 nm to 20 nm.

20. The method of claim 12, wherein the protective material has a thickness in a range from 3 nm to 6 nm.

21. The method of claim 12, wherein the protective material has a thickness in a range from 8 nm to 12 nm.

22. The method of claim 21, wherein the protective material has a thickness of 10 nm.

* * * * *